United States Patent [19]
Clayton et al.

[11] Patent Number: 5,529,913
[45] Date of Patent: Jun. 25, 1996

[54] METHOD OF REMOVING PROTEIN FROM A WATER SOLUBLE GUM AND ENCAPSULATING CELLS WITH THE GUM

[75] Inventors: Heather A. Clayton, Nottingham; Roger F. L. James; Nicholas J. M. London, both of Leicester, all of Great Britain

[73] Assignee: University of Leicester, Leicester, England

[21] Appl. No.: 196,072

[22] PCT Filed: Aug. 14, 1992

[86] PCT No.: PCT/GB92/01511

§ 371 Date: Jun. 22, 1994

§ 102(e) Date: Jun. 22, 1994

[87] PCT Pub. No.: WO93/03710

PCT Pub. Date: Mar. 4, 1993

[30] Foreign Application Priority Data

Aug. 20, 1991 [GB] United Kingdom .................... 9117980
Apr. 1, 1992 [GB] United Kingdom .................... 9207143

[51] Int. Cl.$^6$ .......................... C12N 11/10; C12N 11/04; C07H 1/00; C07H 1/06
[52] U.S. Cl. .................. 435/178; 424/93.7; 435/182; 435/240.22; 536/123.1; 536/127
[58] Field of Search ..................... 435/178, 182, 435/240.22; 436/529; 424/93.7; 530/813; 536/123.1, 127

[56] References Cited

FOREIGN PATENT DOCUMENTS

| | | |
|---|---|---|
| 301777 | 2/1989 | European Pat. Off. . |
| 2094750 | 9/1982 | United Kingdom . |
| 8904657 | 6/1989 | WIPO . |

OTHER PUBLICATIONS

Stryer, Lubert, Biochemistry, 2nd ed. Walt Freeman & Co., N.Y., 1981, pp. 18–38.
Pedersen, et al: "Purification, Characterization, and Immunological Cross–Reactivity of Alginates Produced by Mucoid Pseudomonas Aeruginosa from Patients with Cystic Fibrosis", J. Clin. Microbiol. vol. 27, No. 4, 1989, pp. 691–699.
Goosen et al: "Optimization of Microencapsulation Parameters:Semipermeable Microcapsules as a Bioartificial Pancreas", Biotechnology and Bioengineering, vol. 27, 1985, pp. 146–150.

*Primary Examiner*—David M. Naff
*Attorney, Agent, or Firm*—Cushman Darby & Cushman

[57] ABSTRACT

Contaminating protein is removed from a water soluble gum such as alginate by dialyzing a solution of the gum against a solution of a disulphide bond reducing agent. Purifying the gum by removing antigenic protein improves biocompatability of the gum for making biocompatible capsules containing cells such as mammalian cells. The reducing agent is preferably dithiothreitol, dithioerythritol or 2-mercaptoethanol. Dialyzing is preferably carried out for more than 1 hour and more preferably twice, each time for 2 hours. Cells are encapsulated by forming a suspension of cells in an aqueous solution of the gum, forming droplets from the suspension, gelling the droplets with a multivalent cation, contacting the gelled droplets with a polymer containing cationic groups, such as poly-1-lysine chloride, that cross-link with anionic groups of the gum to form a semi-permeable membrane around the droplets, and coating the membrane with a layer of the dialyzed gum. Islets of Langerhans cells can be encapsulated for implanting to produce insulin. In addition to encapsulating cells, the purified gum can be used in making dressings, swabs, sutures, stitches, controlled or sustained release devices and artificial vascular grafts that come in contact with body fluids such as blood.

40 Claims, No Drawings

METHOD OF REMOVING PROTEIN FROM A WATER SOLUBLE GUM AND ENCAPSULATING CELLS WITH THE GUM

This invention concerns a method of making biocompatible capsules containing cells for implantation into a body which lacks the normal functioning of those cells.

A common problem caused by the implantation of foreign cells and tissue is that of immunological rejection by the recipient. Attempts to overcome this problem commonly involve treating a patient with immunosuppressive drugs. However, this is known to be dangerous as these types of drugs have many side effects. Alternatively, the tissue may be treated in some way so as not to provoke an immune response.

With regard to the latter, means of encapsulating cells, particularly islet cells, have been developed as a method of immunoprotection, using relatively nonantigenic material (Lim and Sum, 1980, Science, 210, 908–910; Lim, U.S. Pat. No. 4,409,331). In their method, a suspension of islet cells in sodium alginate solution was formed into droplets and coated with poly-1-lysine to form a membrane permeable to small molecules such as glucose and insulin, but impermeable to large molecules such as immunoglobulins and the cells of the immune system.

The method was modified by O'Shea et al (1984, Biochimica et Biophysica Acta, 804, 133–136) by coating the capsules with an additional outer layer of sodium alginate in order to further minimise the inflammatory response.

Although some transplantation of encapsulated cells has been moderately successful showing normoglycaemia in diabetic mice two weeks after transplantation of encapsulated islet cells (Calafiore et al, Diabetes Research and Clinical Practice, 1988, 5 suppl 1, S334; Tze and Tai, 1982, Transplantation, 33, 563–564; Ricker and Stockberger, 1986, Diabetes, 35, Suppl 1, 61A), the capsules, on removal, showed infiltration of monocytes and macrophages, ie. severe inflammatory reaction.

A recent study (Clayton et al, Diabetes Research 1990 14 127–132) testing the immune response of rats to implanted empty capsules showed that the composition of the outer layer of the capsule affects the severity of the response, with M-alginate (high mannuronic acid sodium alginate), provoking the least immune response. However, even this reduced response resulted in macrophage and fibroblast infiltration after only 3 weeks.

The present invention overcomes, or at least relieves, the problems aforesaid.

According to the present invention there is provided a method of making biocompatible capsules containing cells comprising the steps:

i) suspending the cells in an aqueous medium containing a pre-dialysed water soluble gum which has plural anionic moieties but is substantially protein free;

ii) forming the suspension into droplets containing the cells;

iii) subjecting the droplets to a solution of multivalent physiologically compatible cations to gel the droplets, encapsulating said cells;

iv) subjecting said gelled droplets to a polymer containing cationic groups which cross link with said anionic groups to form a semi-permeable membrane;

v) coating said semi-permeable membrane with a layer of said pre-dialysed water soluble gum.

The water soluble gum may be sodium or other water soluble alginate, such as potassium alginate.

The alginate may be predialysed with phosphate buffered saline (PBS) containing dithiothreitol (DTT), which helps break down any associated protein by breaking the disulphide bonds present therein. The alginate may be predialysed with PBS containing any chemical capable of reducing disulphide bonds in associated protein, for example, dithioerythritol, 2-mercaptoethanol, and the like.

"Substantially protein free" in this context does not necessarily mean that protein associated with the alginate or other gum is totally removed. Unexpectedly, it is found that it is sufficient if disulphide bonds in the associated protein are broken.

The dithiothreitol concentration may be greater than 0.1 mg/ml, preferably 0.6 mg/ml, other chemicals in corresponding amounts.

The alginate may be dialysed for more than 1 hour, preferably twice for 2 hours against PBS containing DTT, or any chemical capable of reducing disulphide bonds, and against PBS alone for more than 65 hours, to ensure efficient removal of contaminating antigenic protein.

The cells may be suspended in normal saline containing the purified alginate.

The cell suspension may contain more than 1% w/v of the pre-dialysed, purified alginate, preferably 1.5% w/v.

The cells to be encapsulated may be mammalian cells such as insulin secreting islet of Langerhans cells, useful for implantation into diabetic patients.

Where islets of Langerhans cells are to be used for transplantation, 1 to 2 whole islets may be encapsulated.

The suspension of cells and alginate may be formed into droplets between 0.3 and 1.0 mm in diameter by dropping from a syringe into a solution containing cations which gels the droplets, encapsulating said cells.

The solution containing cations may be calcium chloride at a concentration greater than 0.5% w/v, preferably 1.1% w/v.

The polymer containing cationic groups to which the gelled droplets are subjected to may be poly-1-lysine chloride.

The molecular weight of the poly-1-lysine chloride may be greater than 3000, preferably 20,000

The poly-1-lysine chloride may be dissolved in normal saline solution at a concentration of more than 0.01% w/v, preferably at a concentration of 0.05% w/v.

The gelled droplets may be subjected to the poly-1-lysine chloride solution for more than 1 minute to form a semi-permeable membrane, preferably for 6 minutes.

The semi-permeable membrane thus formed may be coated with a layer of pre-dialysed water soluble gum by subjecting the semi-permeable membrane to a solution containing more than 0.1% w/v of the gum for more than 1 minute.

The solution may contain 0.15% w/v pre-dialysed sodium alginate in normal saline.

The semi-permeable membrane may be subjected to the solution for 4 minutes.

The invention also comprises a biocompatible capsule containing cells made by the method described herein.

The invention also comprises a method for purifying water soluble gums such as water soluble alginates such as sodium alginate and potassium alginate comprising predialysing the gum with a solution containing a disulphide bond reducing agent, and also comprises a gum purified by such method.

By purification in this context is meant eliminating or substantially reducing bio-activity due to associated proteinaceous material to render the gum (assumed per se biocompatible) sufficiently biocompatible for the contemplated end use.

In addition to its utility for encapsulating islets of Langerhans cells for implantation into diabetic patients, alginate (or other biocompatible water soluble gum) purified by the method of the invention is useful in any situation where an alginate is in direct contact with body fluids, including blood.

Where dressings, swabs, sutures and stitches and the like are introduced into the body during surgery and left there post-operation, alginate purified by the method of the invention is particularly useful. Dressings may be woven or knitted fabrics constructed from alginate fibres. They might also be a non-woven fabric pad made from teased alginate fibres, such as cotton wool, or a moist sheet or formed slab or shape made from an alginate gel or film. Swabs may be non-woven assemblies of alginate fibres. Sutures and stitches may be made from single or multiple filament spun threads of alginate.

Similar dressings that are used to cover open surface wounds may also be prepared using alginate purified by the method of the invention. Alginate dressings are used as hemostats and for moist wound management. Alginate powder is also used as a hemostat for open wounds (e.g. to promote fast clotting for sports use).

Dressings and patches that are implanted below the skin and which contain active ingredients may also be prepared using alginate purified by the method of the invention.

Controlled or sustained release devices which are implanted into the body or injected rather than going through the normal digestive system may also be prepared using alginate purified by the method of the invention.

Alginate-containing capsules or other devices, including devices implanted into the body, whereby the alginate provides a membrane to sieve by molecular size and control the flow of chemicals into and out of the capsule, may be prepared using alginate purified by the method of the invention.

These alginates may also be used for coating artificial vascular grafts (e.g. Dacron (RTM) grafts) which are implanted into a patient.

The invention will be further apparent from the following description, with reference to the experiment detailed herein, which shows, by way of example only, one form of the method of making biocompatible capsules containing cells embodying the invention.

Protocol for making biocompatible capsules containing islet of Langerhans cells

1. Purification of sodium alginate.

Sodium alginate (supplied by Kelco International) was made up to 1.5% (w/v) solution in normal saline (0.9% w/v sodium chloride). 10 ml of this solution was put into a dialysis sac (Sigma, Cat. No. 250-11), which retains proteins with a molecular weight greater than 12,000. The sodium alginate was dialysed against phosphate buffered saline (PBS; 140 mM NaCl, 35 mM $K_2PO_4$, pH 7.3) containing dithiothreitol (DTT) for 2 hours and dialysed for a further 2 hours against fresh PBS+DTT, after which it was dialysed against PBS alone for a total of approximately 70 hours, with fresh PBS at 1 and 65 hours.

The sodium alginate was analysed for the presence of contaminating antigenic protein by polyacrylamide gel electrophoresis. This analysis confirmed that the sodium alginate was indeed protein free. Protein was not removed from sodium alginate when it was dialysed against PBS with no DTT in an identical procedure to that stated above. This suggests that the DTT is essential for the efficient removal of protein from sodium alginate.

2. Protocol for encapsulation

Islets were removed from either rats or humans and suspended in a 1.5% w/v solution of purified (ie. protein free) sodium alginate in normal saline. The solution was mixed and drawn up into a 2 ml syringe via a quill and attached to an infusion pump. The infusion pump was set to the desired rate, normally 1 ml/min, and the drops of sodium alginate/islet suspension dropped into a 1.1% w/v solution of calcium chloride from a height of 7 cm so that the drops would be spherical on entering the calcium chloride solution. On entering the solution the sodium alginate gels to encapsulate the islets, usually containing 1–2 islets per capsule, the capsules being in the range 0.3–1.0 mm in diameter. The gelled capsules are washed with 25 ml volumes of 0.55% $CaCl_2$; 0.27% $CaCl_2$; 0.85% NaCl. The capsules are then placed in 0.1% CHES (pH 8.2 in NaCl) for 3 minutes before being suspended and agitated in 25 ml of 0.05% poly-1-lysine hydrochloride (MW 20,000) in NaCl for 6 minutes. The cationic groups on the poly-1-lysine crosslink with the anionic groups on the sodium alginate capsule to form a semi-permeable membrane. The molecular weight of the poly-1-lysine is selected to form a semi-permeable membrane of the desired permeability, in this case sufficient to allow out insulin but not to allow in immunoglobulins and other cells of the immune system.

The capsules are then washed with 25 ml of 0.1% CHES and a further 25 ml of 0.85% NaCl before an outer coat of purified sodium alginate is added to the capsules in order to further increase their biocompatability. This is done by suspending the washed capsules in a 0.15% w/v sodium alginate solution (in normal NaCl) for 4 minutes with agitation. The coated capsules are then washed with 25 ml 0.9% NaCl, suspended in 10 ml of 55 mM sodium citrate for 6 minutes, washed again with 25 ml 0.9% NaCl, washed twice with cell culture medium before being suspended in cell culture medium prior to implantation.

Initial results using implanted encapsulated islets in rats confirmed the greatly increased biocompatability of the capsules using "purified" sodium alginate. This gives great hope for the future implantation of human islets into diabetic patients, which would mean that they could produce their own insulin, eliminating the need for daily injections.

The enhanced glucose control provided by transplanted islets compared to injected insulin may potentially avoid the complications such as blindness and kidney failure which affect a proportion of insulin-dependent diabetic patients.

We claim:

1. A method for substantially removing protein from water soluble gums containing protein comprising dialyzing a solution of water-soluble gum containing protein against a solution containing a disulphide bond reducing agent for a period of time sufficient to substantially remove protein from the gum.

2. A method according to claim 1, in which the disulphide bond reducing agent is contained in a phosphate buffered saline.

3. A method according to claim 1, in which the reducing agent comprises dithiothreitol.

4. A method according to claim 1, in which the reducing agent comprises dithioerythritol.

5. A method according to claim 1, in which the reducing agent comprises 2-mercaptoethanol.

6. A method according to claim 3, in which the dithiothreitol concentration is greater than 0.1 mg/ml.

7. A method according to claim 6, in which the dithiothreitol concentration is 0.6 mg/ml.

8. A method according to claim 1, in which said dialyzing is carried out at least once for more than one hour.

9. A method according to claim 8, in which said dialyzing is carried out twice, each time for 2 hours.

10. A method according to claim 1, followed by an analysis confirming that the water-soluble gum is substantially protein free.

11. A method according to claim 10, in which the analysis is carried out by polyacrylamide gel electrophoresis.

12. A method of making biocompatible capsules containing cells comprising the steps:

i) dialyzing a solution of a water soluble gum which has plural anionic groups and contains protein against a solution of a disulphide bond reducing agent for a period of time sufficient to make the water soluble gum substantially protein free, and suspending cells in an aqueous medium containing the dialyzed water soluble gum to produce a cell suspension;

ii) forming the suspension into droplets containing the cells;

iii) subjecting the droplets to a solution of multivalent physiologically compatible cations to gel the droplets, encapsulating said cells;

iv) subjecting said gelled droplets to a solution of a polymer containing cationic groups which cross link with said anionic groups to form a semi-permeable membrane; and v) coating said semi-permeable membrane with a layer of said dialyzed water soluble gum.

13. A method according to claim 12, wherein the water soluble gum is a water-soluble alginate.

14. A method according to claim 12, wherein the reducing agent comprises dithiothreitol.

15. A method according to claim 12, wherein the reducing agent comprises dithioerythritol.

16. A method according to claim 12, wherein the reducing agent comprises 2-mercaptoethanol.

17. A method according to claim 14, wherein the dithiothreitol concentration is greater than 0.1 mg/ml.

18. A method according to claim 17, wherein the dithiothreitol concentration is 0.6 mg/ml.

19. A method according to claim 13, wherein said dialyzing is carried out at least once for more than 1 hour.

20. A method according to claim 19, wherein said dialyzing is carried out twice, each time for 2 hours.

21. A method according to claim 12, wherein the aqueous medium is normal saline.

22. A method according to claim 13, wherein the cell suspension contains more than 1% w/v of said water-soluble alginate.

23. A method according to claim 22, wherein the cell suspension contains 1.5% w/v of said water-soluble alginate.

24. A method according to claim 12, wherein the cells are mammalian cells.

25. A method according to claim 24, wherein the cells are islets of Langerhans cells.

26. A method according to claim 25, wherein 1 to 2 islets are encapsulated.

27. A method according to claim 12, wherein the suspension is formed into droplets with a syringe and the gelled droplets are between 0.3 and 1.0 mm in diameter.

28. A method according to claim 27, wherein the solution containing cations is calcium chloride at a concentration greater than 0.5% w/v.

29. A method according to claim 28, wherein the calcium chloride solution is 1.1% w/v.

30. A method according to claim 12, wherein the polymer containing cationic groups is poly-1-lysine chloride.

31. A method according to claim 30, wherein the molecular weight of the poly-1-lysine chloride is greater than 3000.

32. A method according to claim 31, wherein the molecular weight of the poly-1-lysine chloride is 20,000.

33. A method according to claim 30, wherein the poly-1-lysine chloride is in normal saline solution at a concentration of more than 0.01% w/v.

34. A method according to claim 33, wherein the concentration of poly-1-lysine chloride is 0.05% w/v.

35. A method according to claim 12, wherein the polymer is poly-1-lysine chloride and the gelled droplets are subjected to the poly-1-lysine chloride solution for more than 1 minute.

36. A method according to claim 35, wherein the gelled droplets are subjected to the poly-1-lysine chloride solution for 6 minutes.

37. A method according to claim 12, wherein the semi-permeable membrane is coated with a layer of said dialyzed water soluble gum by subjecting the semi-permeable membrane to a solution containing more than 0.1% w/v of said dialyzed water-soluble gum for more than 1 minute.

38. A method according to claim 37, wherein the solution contains 0.15% wt/v of said dialyzed water-soluble gum.

39. A method according to claim 37, wherein the semi-permeable membrane is subjected to the solution of said dialyzed water-soluble gum for 4 minutes.

40. A biocompatible capsule containing cells made by the method described in claim 12.

* * * * *